United States Patent [19]
Joffre

[11] Patent Number: 5,922,909
[45] Date of Patent: Jul. 13, 1999

[54] PROCESS FOR THE SELECTIVE CONTROL OF ZWITTERIONIC AMPHOTERIC COMPOSITIONS

[75] Inventor: Lawrence J. Joffre, Bethel, Conn.

[73] Assignee: Akzo Nobel nv, Arnhem, Netherlands

[21] Appl. No.: 09/052,288

[22] Filed: Mar. 31, 1998

[51] Int. Cl.$^6$ ...................... C07C 209/60; C07C 229/12; C07C 229/24
[52] U.S. Cl. ............................................. 562/553; 562/571
[58] Field of Search ...................... 562/553, 571

[56] References Cited

U.S. PATENT DOCUMENTS

| | | | |
|---|---|---|---|
| 2,195,974 | 4/1940 | Roppe et al. | 260/534 |
| 2,468,012 | 4/1949 | Isbell | 260/534 |
| 2,619,467 | 11/1952 | Isbell | 252/152 |
| 2,781,372 | 2/1957 | Mannheimer | 562/553 |
| 2,810,752 | 10/1957 | Freese | 562/553 |
| 2,811,549 | 10/1957 | Aelony | 562/553 |
| 2,816,911 | 12/1957 | Aelony | 260/482 |
| 2,816,920 | 12/1957 | Andersen | 562/553 |
| 3,133,816 | 5/1964 | Ben-Ezra | 96/94 |
| 4,691,049 | 9/1987 | Doll et al. | 562/553 |
| 5,281,749 | 1/1994 | Uphues et al. | 562/553 |
| 5,597,513 | 1/1997 | Cohen | 252/358 |

OTHER PUBLICATIONS

Chemicals Abstract, DT–2054659, dated May 10, 1972.
John P. Parke, "Soaps containing nonionic cleansing agents". Unilever N.V., Germ. 1,011,555, Jul. 4, 1957.
Abstract, Cohen E. US 5597513–A, date Jan. 28, 1997.
Abstract, Miyoshi Yushikk, J6 1293–959–A, Dec. 24, 1986.
Chem Fab Stockhausen, EP–265–818–A, dated May 4, 1988.
Abstract, Tian, Zailong, "Study of N–alky beta –aminopropionate zwitterionic surfactant. Part I, Synthesis and performance test". Chinese 553243, (1991).
Abstract, Hideo Marumo, Makoto Takai, Minoru Saito, Morio Ninomiya, "The preparation of metal salts of alanine, amidoamine, and diamine surface–active agents". 69(7) Kogy Kagaku Zasshi. 1306–9 (1966).
Limanov, V. E., Sobol, A. F., Vornotsova, L. M., "Synthesis and antibacterial properties of ampholytic preparations based on dodecylamine", 34 *Synthesis of Amino Acids, Peptides, and Proteins* (1971).

*Primary Examiner*—Brian M. Burn
*Assistant Examiner*—Brian J. Davis
*Attorney, Agent, or Firm*—Ralph J. Mancini

[57] ABSTRACT

A selective process for the preparation of N-alkyl-beta aminopropionic acids (1) and N-alkyl-beta-iminodipropionic acids (II)

$$RNHC_2H_4COOH \tag{I}$$

$$RNH(C_2H_4COOH)_2 \tag{II}$$

wherein R is a $C_8$ to $C_{24}$ hydrocarbon, said process comprising reacting an alpha, beta-unsaturated carboxylic acid in aqueous media with the corresponding primary amine of the formula $R_1NH_2$ wherein $R_1$ is a fatty group having 8 to 24 carbon atoms, in the presence of an organic or inorganic base having a pKb of >1<15, whereby the pH of the reaction is maintained in a range of from about 3.5 to about 5.

18 Claims, 2 Drawing Sheets

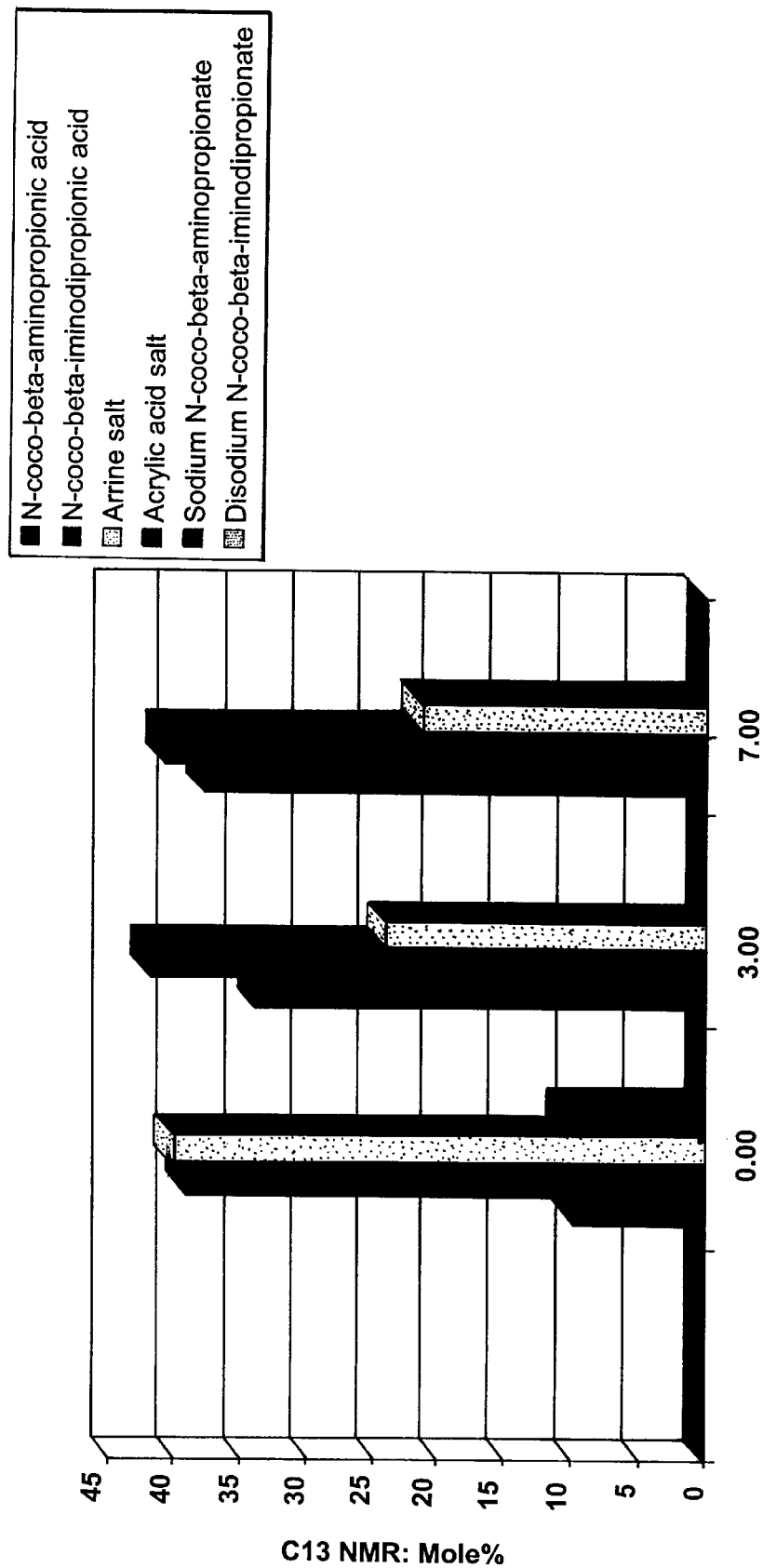

PROCESS FOR THE SELECTIVE CONTROL OF ZWITTERIONIC AMPHOTERIC COMPOSITIONS

FIELD OF THE INVENTION

The present invention generally relates to a process for the selective control of zwitterionic amphoteric surfactant compositions.

BACKGROUND OF THE INVENTION

Zwitterionic amphoteric surfactant fire useful and versatile adjuncts in applications such as cosmetics, shampoo, detergents, industrial cleaners, emulsifiers, textile additives, aerosol packaging and the like. The prior art generally recognizes that such amphoterics can be prepared in accordance with the following reaction scheme.

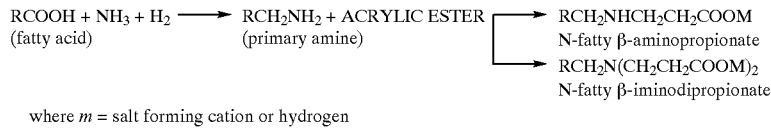

where m = salt forming cation or hydrogen

For example, U.S. Pat. No. 2,195,974 describes a process for producing aminocarboxylic acids which comprises reacting acrylic acid or methacrylic acid with ammonia and/or organic derivatives of ammonia having at least one $NH_2$ group at a temperature of between 40 and 150° C. in the presence of water.

U.S. Pat. No. 2,816,911 discloses a process for preparing compounds of the formula: $RNHC_2H_4COOR_1$, wherein R is an aliphatic hydro-carbon group containing 8–22 carbon atoms and $R_1$ is a lower alkyl group containing from 1–4 carbon atoms. The process comprises reacting the corresponding amine $RNH_2$ with the corresponding lower alkyl acrylate ester, said ester being employed in an excess of from 10–30% at temperatures within the range of 50–120° C.

U.S. Pat. No. 2,468,012 discloses a process of producing a compound of the formula $RNHCH_2CH_2COOX$ in which R is an aliphatic hydrocarbon group containing from 10 to 18 carbon atoms and X is selected from the group consisting of hydrogen and a salt forming radical. The process comprises reacting the amine, $RNH_2$ with an ester of acrylic acid in the absence of a solvent and in the absence of a catalyst to form a beta amino ester, and replacing the ester group with a hydrophilic group.

Finally, U.S. Pat. No. 3,133,816 discloses the preparation of amphoteric surfactants by condensing at 25–30° C., a primary amine containing from 8 to 20 carbon atoms with methyl acrylate to form the β-alkylaminopropionate. The methyl ester is hydrolyzed to an acid or converted to the alkali or organic amine salts by the conventional method of saponification. The secondary amine is obtained by the use of molar proportions whereas the tertiary amine is obtained by using at least two molar equivalents of the acid derivatives.

Because of the special uses in detergents and cosmetics products, it is highly desirable that the surfactant have a low free amine content and a low free acid content along with good color. Further, it is known in the prior art that the performance of Zwitterionic amphoterics which contain one carboxyl group exhibit substantially different properties, i.e., hydrophobicity compared to those having two carboxyl groups, i.e., hydrophobicity. Thus, it is highly desirable to improve the state of the art by providing a process which allows for the preparation of amphoteric surfactants having low free amine content, low free acid content, good color, and low odor, which is selective thus allowing one to control the specificity towards one formation species over the other. In addition, the reaction of the primary amine and the alpha, beta-unsaturated carboxylic acid in an equimolar ratio does not exclusively produce one product, but results in a distribution of products, whereby the object of the present invention is to effect control over this distribution.

Accordingly, it is in object of the present invention to provide a process for the preparation of aqueous solutions of Zwitterionic amphoteric surfactants having low free amine and free acid content along with good color and odor.

It is a further object of the present invention to provide a process for the selective control of aqueous solutions of Zwitterionic amphoteric surfactant compositions depending on the end-use.

These and other objects are realized by the process of the present invention.

SUMMARY OF THE INVENTION

The present invention generally relates to a selective process for the preparation of N-alkyl-beta aminopropionic acids (I) or N-alkyl-beta-iminodipropionic acids (II)

$$RNHC_2H_4COOH \tag{I}$$

$$RNH(C_2H_4COOH)_2 \tag{II}$$

wherein R is a $C_8$ to $C_{24}$ hydrocarbon, said process comprising reacting an alpha, beta-unsaturated carboxylic acid in aqueous media with the (corresponding primary amine of the formula $R_1NH_2$ wherein $R_1$ is a fatty group having 8 to 24 carbon atoms, in the presence of an organic or inorganic base having a pKb of >1<15, whereby the pH of the reaction is maintained in a range of from about 3.5 to about 5.

DETAILED DESCRIPTION OF THE FIGURES

FIG. 2 shows the component distributions @pH 4.51 (0.02 moles of sodium hydroxide).

DETAILED DESCRIPTION OF THE INVENTION

Figure 1:
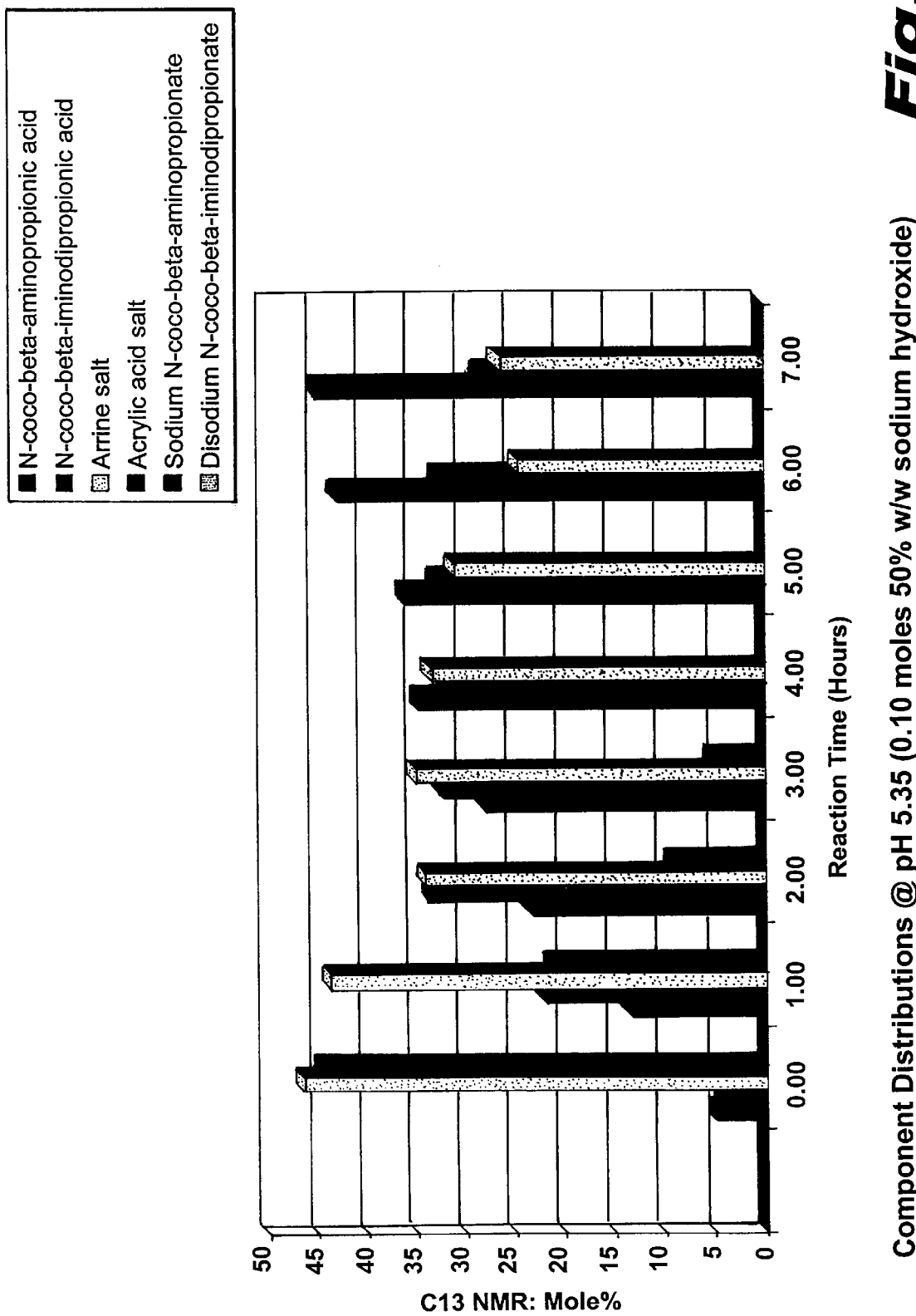
FIG. 1 depicts the component distributions @pH 5.35 (0.10 moles sodium hydroxide).

The present invention generally relates to a process for the selective control of zwitterionic amphoteric surfactants. By zwitterionic amphoteric, it is meant that both amino and carboxyl functionalities are contained in the structure of the compound in their free carboxylic acid form. Examples include but are not limited to: N-alkyl-beta-aminopropionic acid(I) and N-alkyl-beta-iminodipropionic acid forms (II)

I) $RNHCH_2CH_2COOH$

II) RN(CH$_2$CH$_2$COOH)$_2$ wherein R is a C$_8$–C$_{24}$ hydrocarbon group. Preferably, R is a straight or branched chain, substituted or unsubstituted, saturated or unsaturated, aliphatic or cyclic alkyl group having from 8 to 24 carbon atoms. The fatty or aliphatic alkyl groups may be restricted to a single chain length or may be of mixed chain lengths.

Depending on the end-use application and desired hydrophobicity/hydrophobicity, one may prefer to utilize either the mono-adduct or the di-adduct. The present process allows for the selective formation of one over the other.

The process of the invention generally comprises reacting, at ambient or elevated temperatures and ambient pressure an alpha, beta- unsaturated carboxylic acid in aqueous media with a primary amine in the presence of an inorganic and/or organic base of pKb>1<15, which is preferably sodium hydroxide. The base serves to increase the equilibrium concentration of free amine within the system.

Regarding the above process, applicants have unexpectedly found that mono-adduct selectivity is favored by adjusting the system to a pH in the range of from about 4.5 to about 7, preferably about 5 to about 7 by addition of an appropriate amount of base, e.g., sodium hydroxide, to the system.

Additionally, applicants have found that di-adduct selectivity is favored by adjusting the system pH to a range of from about 3.5 to about 5, preferably from about 4 to about 5, by addition of an appropriate amount of base, e.g., sodium hydroxide, to the system. In effect, lowering the pH of the system essentially increases the reactivity of the carboxylic acid towards to di-species.

It is believed that in prior art processes, which are generally performed at a pH of greater than 7, the reaction time is prolonged thereby limiting both mono- and di-adduct conversion. This is believed to occur because the sodium extracts a proton from the carboxylic acid delocalizing the resonance stabilization of the transition state species, thereby decreasing the reactivity of the olefin, the net results of which produces product where enhanced levels of free amine and the anionic carboxylic salt of the mono- and di-acids are the main components.

Within the constraints of a molar stoichiometry of 1.00 mole of primary amine to 1.00–1.10 moles of an alpha,beta-unsaturated carboxylic acid, three predominant reaction species were found to be present in equilibrium with one another; N-alkyl-beta aminopropionic acid, N-alkyl-beta-iminodipropionic acid and amine salt. In a system where such a distribution exists, one species is considered to be dominant over the others (i.e. prior art—exhibiting greater hydrophobicity in the case of the amino adduct in contrast with greater hydrophobicity in the case of the iminodi-adduct) when the said component comprises greater than 40% of the mixture. In the examples that follow, adjustments to the pH with sodium hydroxide to the acrylic acid monomer+water mixture prior to the addition of the primary amine shifted the product distribution in favor of one particular adduct. The following chart documents this point:

| pH Range | Major Reaction Species | Minor Reaction Species |
| --- | --- | --- |
| <4 | Cationic amine salt | Iminodipropionic acid Aminopropionic acid |
| 4–5 | Iminodipropionic acid | Aminopropionic acid |
| 5–7 | Aminopropionic acid | Iminodipropionic acid |
| >7 | Anionic carboxylic salt of the amino and iminodipropionic acid | Free amine |

In addition to the effect of pH on the specificity of the reaction towards the formation of the N-alkyl-beta-aminopropionic acid and the N-alkyl-beta-iminodipropionic acid, we have also discovered that increasing the alkyl chain length also increased the selectivity towards the N-alkyl-beta-aminopropionic acid species.

The term alpha, beta-unsaturated mono- and di- carboxylic acids as used herein shall include but not be limited to acids such as acrylic acid, crotonic acid, isocrotonic acid, methacrylic acid, sorbic acid, cinnamic acid, maleic acid, fumeric acid, angelic acid, itaconic acid and mixtures thereof.

The fatty amines which may be employed in the present process are primary fatty amines having a fatty group containing 8–24 carbon atoms. These may be single isolated fatty amines or may be mixed fatty amines derived from the fatty acids of a fat or oil or from any selected fraction thereof. The amines may be either saturated or unsaturated. Preferred examples of the primary amines which can be employed in the process of the present invention include but are not limited to n-dodecylamine, n-hexadecylamine, n-octyldecylamine, cocoamine, tallowamine, hydrogenated tallowamine, partially hydrogenated tallowamine, oleylamine, erucylamine, behenylamine, lignocyrlamine and mixture thereof.

The organic or inorganic bases employed in the present reaction preferably have a pKb of >1<15. Suitable bases include but are not limited to ammonia, hydroxylamine, diethylamine, methylamine, n-butylamine, glycine, aniline, alkali metal hydroxides wherein the cation is sodium, lithium, barium, magnesium, calcium, or potassium, metal oxides such as sodium, magnesium, calcium, barium oxides; and mixtures and combinations of same. Alkali metal hydroxides are the preferred bases, with sodium hydroxide being the preferred alkali metal hydroxide.

In carrying on the reaction, the amine and the acid are mixed, the acid being employed in a molar excess of from about 3 to about 40, more preferably, from about 3 to about 20. A most preferred molar excess of the acid is from about 4 to about 10. The reaction mixture is heated and agitated at temperatures within the approximate range of 50 to 120° C. The time period will vary depending upon the temperature and the particular excess of acid employed. At temperatures of 80 to 100° C. up to 8 hours is required.

If one desires to move selectivity towards formation of the mono-adduct, then the pH of the system should be maintained within a range of from about 4.0 to about 7.0, preferably from about 5 to about 7. The product obtained by the process of the present invention typically contains at least 35% mono-adduct, preferably at least 40% mono-adduct, with a 40% mono-,30% di-, and 30% amine salt product distribution being typical.

Conversely, if one desires to push tie reaction towards formation of the di-adduct, then the pH of the system should be adjusted to be in the range of from about 3.5 to about 5.0, preferably about 4.0 to about 5.0.

The invention will now be illustrated by the following nonlimiting examples.

Internal Procedure for the Determination of the Cloud Point for Amino Acid Amphoterics, Betaines, Imidazoline Derived Amphoterics, and Alkyl Poly Amino Acid Amphoterics This method covers the determination of the solubility inversion temperature or "Cloud Point" of Amino Acid Amphoterics, Betaines, Imidazoline Derived Amphoterics, and Alkyl Poly Amino Acid Amphoterics. The presence of salts and bases will specifically lower the cloud point of the surfactant, whereas, acids will raise the cloud point. As levels of free primary amine and its respective amine salt reduce, an increase in cloud point will be exhibited until reaction equilibrium is achieved. The present method is based upon heating a mixture of the following ingredients to the temperature at which the solution becomes cloudy.
Formulation:
1. 8% w/w aqueous sodium hydroxide: 60 gm
2. Polyoxyethylene—(9)—nonylphenyl ether 3 gm
3. Amino acid amphoteric 6 gm

EXAMPLE 1

Based Upon Molar Stoichiometry of 1.00 Moles Primary Amine: 1.05 Moles Alpha, Beta- Unsaturated Carboxylic Acid 750 g (41.67 moles) of tap water, 151.4 g (2.10 moles) of 99.0% acrylic acid, and 8.0 g (0.10 moles) of 50% w/w aqueous sodium hydroxide were charged to a 2.0 liter glass resin kettle equipped with an electric stirrer and fitted with a Allihn-type water-cooled condenser. While slowly stirring the system, 394.6 g (2.00 moles) of distilled cocoalkylamine was added to the aforementioned mixture over a period of one hour. The pH of the reaction mixture at this stage was 5.35. The contents of the resin kettle were heated to 90° C. After seven hours of digestion at 90° C., the reaction was considered at completion when its cloud point elevation was at a maximum temperature. The final pH of the reaction mixture at completion of the digestion period was 6.10. The resin kettle was cooled and emptied. The contents were shown to contain by $C^{13}$NMR 45.0 mole % N-coco-beta-aminopropionic acid, 28.40 mole % N-coco-beta-iminodipropionic and 26.6 mole % amine salt.

Table 1 tabulates the selectivity towards the N-coco-beta-aminopropionic acid species @ pH 5.35 (0.10 moles Sodium Hydroxide) while FIG. 1 graphically depicts said selectivity.

EXAMPLE 2

As Example 1, but the concentration of 50% w/w sodium hydroxide was reduced to 1.60 g (0.02 moles) to a reaction system pH of 4.51. The final pH after seven hours of digestion at 90° C. was 4.87. The component compositions shown by $C^{13}$NMR indicated the selectivity was shifted towards the N-coco-beta-iminodipropionic acid as 40.80 mole % N-coco-beta-iminodipropionic acid, 37.70 mole % N-coco-beta-aminopropionic acid, and 21.50 mole % amine salt.

Table 2 tabulates the selectivity towards the N-coco-beta-iminodipropionic acid species @ pH 4.51 (0.02 moles NaOH) while FIG. 2 graphically depicts said selectivity.

TABLE 2

The Selectivity Towards the N-coco-beta-iminodipropionic acid Species @ pH 4.51
(0.02 moles 50% w/w sodium hydroxide)

| Reaction Time [Hours] | N-coco-beta- aminopropionic acid | N-coco-beta- iminodipropionic acid | Amine salt | Acrylic acid salt | Sodium N-coco-beta- aminopropionate | Disodium N-coco-beta- iminodipropionate |
|---|---|---|---|---|---|---|
| 0.00 | 9.90 | 39.40 | 40.20 | 10.50 | 0.00 | 0.00 |
| 3.00 | 34.00 | 41.80 | 24.20 | 0.00 | 0.00 | 0.00 |
| 7.00 | 37.70 | 40.80 | 21.50 | 0.00 | 0.00 | 0.00 |

Data acquired by $C^{13}$ NMR in mole %

EXAMPLE 3

In addition to the effect of pH on the specificity of the N-alkyl-beta-aminopropionic acid and N-alkyl-beta-iminodipropionic acid, we have discovered that increasing the alkyl chainlength is associated with increasing selectivity towards the N-alkyl-beta-aminopropionic acid species. These series of individual reactions employed distilled n-dodecylamine in the former, and distilled, hydrogenated tallowanine in the latter.

As in Example 1, but substituting the distilled n-dodecylamine for the distilled cocoamine and correcting for the difference in molecular weight while maintaining a system pH of 5.70. The final component assignments by $C^{13}$NMR identified 37.70 mole % N-dodecyl-beta-aminopropionic acid, 29.30 mole % N-dodecyl-beta-iminodipropionic acid, 31.20 mole % amine salt, and 1.80% acrylic acid salt after the standard seven hours of reaction time. This data resembled the cocoalkyl composition after five hours of reaction time—a significant depression in the reaction rate when compared against the N-alkyl-beta-aminopropionic acid species.

TABLE 1

The Selectivity Towards the N-coco-beta-aminopropionic acid Species @ pH 5.35
(0.10 moles 50% w/w sodium hydroxide)

| Reaction Time [Hours] | N-coco-beta- aminopropionic acid | N-coco-beta- iminodipropionic acid | Amine salt | Acrylic acid salt | Sodium N-coco-beta- aminopropionate | Disodium N-coco-beta- iminodipropionate |
|---|---|---|---|---|---|---|
| 0.00 | 5.00 | 4.30 | 46.30 | 44.40 | 0.00 | 0.00 |
| 1.00 | 13.40 | 21.90 | 43.70 | 21.00 | 0.00 | 0.00 |
| 2.00 | 23.40 | 33.50 | 34.00 | 9.10 | 0.00 | 0.00 |
| 3.00 | 2S.00 | 32.00 | 34.90 | 5.10 | 0.00 | 0.00 |
| 4.00 | 34.50 | 32.20 | 33.30 | 0.00 | 0.00 | 0.00 |
| 5.00 | 36.00 | 33.00 | 31.00 | 0.00 | 0.00 | 0.00 |
| 6.00 | 42.70 | 32.70 | 24.60 | 0.00 | 0.00 | 0.00 |
| 7.00 | 45.00 | 28.40 | 26.60 | 0.00 | 0.00 | 0.00 |

Data acquired by $C^{13}$ NMR in Mole %

As in Example 1, the procedure was repeated except that distilled, hydrogenated tallowamine was used instead of the distilled cocoamine; similarly correcting for the difference in molecular weight while maintaining a system pH of 5.24. The final component assignments by $C^{13}$NMR identified 55.90 mole % N-hydrogenated, tallow-beta-aminopropionic acid, 20.50 mole % N-hydrogenated, tallow-beta-iminodipropionic acid, and 23.60 mole % amine salt after the standard seven hours of reaction time—a significant elevation in the reaction rate when compared against the N-alkyl-beta-aminopropionic acid species.

Based on the experimental evidence complied, the data clearly suggests that the rate of formation of the N-alkyl-beta-aminopropionic acid increases with increasing chain length.

EXAMPLE 4

Based Upon Molar Stoichiometry of 1.00 Moles Primary Amine: 1.10 Moles Alpha,Beta-Unsaturated Carboxylic Acid A 2.0 liter, 4-neck glass resin kettle was equipped with an electric stirrer, thermowell with thermocouple and temperature controller, an Allihn water-cooled reflux condenser and a separatory funnel for adding the primary amine dropwise.

In the resin kettle were placed 750.0 g (41.67 moles) of tap water, 158.6 g (2.20 moles) of 99.0% acrylic acid, and 16.0 g (0.20 moles) of 50% w/w aqueous sodium hydroxide. While slowly stirring the mixture, 394.6 g (2.00 moles) of distilled cocoalkylamine was added dropwise at such a rate to maintain a one hour addition time sequence. The pH of the reaction mass at this stage was 5.52. The contents of the resin kettle were heated to 90 C. After seven hours at 90° C., the reaction was considered at completion when its cloud point elevation was at a maximum temperature. The final pH of the reaction mixture at completion of the digestion was 6.20. The resin kettle was then cooled to room temperature and discharged. The product was analysed by $C^{13}$NMR. The results of this analysis indicated 42.30 mole % N-coco-beta-aminopropionic acid, 27.80 mole % N-coco-beta-iminodipropionic acid and 29.90 mole % amine salt.

Example 1 and Example 4 clearly show that preferential selectivity towards the N-fattyalkyl-beta-aminopropionic acid was achieved within a stoichiometric range of 1.00 mole of primary amine to 1.00–1.10 moles of an alpha,beta-unsaturated carboxylic acid while restricting the pH of the reaction media within a range of 5–7.

EXAMPLE 5

Reaction Time Dependence Optimization

As Example 1, the product was further digested for a period of 48 hours at 75° C, analysis by $C^{13}$NMR indicated 53.70 mole % N-coco-beta-aminopropionic acid, 23.70 mole % N-coco-beta-iminodipropionic acid, 21.00 mole % protonated amine, and 1.60 mole % acrylic acid salt.

In Examples 1 through 5, it therefore has been found that the said process and the resultant amino acid amphoteric adducts are favored by time and thermodynamics in addition to pH sensitivity.

We claim:

1. A selective process for the preparation of N-alkyl-beta-aminopropionic acid (I)

$$RNHC_2H_4COOH \quad (I)$$

wherein R is a $C_8$ to $C_{24}$ hydrocarbon, said process comprising reacting, in aqueous media, an alpha, beta- unsaturated carboxylic acid employed in a molar excess of from about 5 to about 30 with the corresponding primary amine of the formula $R_1NH2$ wherein $R_1$ is a fatty group having 8 to 24 carbon atoms, in the presence of an organic or inorganic base having a pKb of >1<15, whereby said acid is initially added to said aqueous media, the molar excess of acid is neutralized by addition of said base, followed by addition of said amine over time, the pH of the reaction being maintained in a range of from about 4.0 to about 7.

2. The process of claim 1 wherein the pH is maintained in a range of from about 5 to about 7.

3. The process of claim 1 wherein the acid is selected from the group consisting of acrylic acid, crotonic acid, isocrotonic acid, methacrylic acid, sorbic acid, cinnamic acid, maleic acid, fumeric acid, angelic acid, itaconic acid and mixtures thereof.

4. The process of claim 1 wherein $R_1$ is a fatty group having from 12 to 22 carbon atoms.

5. The process of claim 1 wherein the amino is selected from the group consisting of n-dodecylamine, n-hexadecylamine, n-octyldecylamine, cocoamine, tallowamine, hydrogenated tallowamine, partially hydrogenated tallowamine, oleylamine, erucylamine, behenylamine, lignocyrlamine and mixtures thereof.

6. The process of claim 1 wherein the base is selected from the group ammonia, hydroxylamine, diethylamine, methylamine, n-butylamine, glycine, aniline, alkali metal hydroxides, metal oxides and mixtures thereof.

7. The process of claim 1 wherein the reaction is conducted at a pressure of from atmospheric to about 100 psi.

8. The process of claim 6 wherein the pressure is from about atmospheric to about 50 psi.

9. The process of claim 1 wherein the acid is acrylic acid, the base is sodium hydroxide and the amine is cocoamine.

10. A composition prepared in accordance with the process of claim 1 which comprises greater than about 35 wt % N-alkyl-beta aminopropionic acid (I) based on the total dissolved solids, N-alkyl-beta iminodipropionic acids (II) and amine salt,

$$RNHC_2H_4COOH \quad (I)$$

$$RNH(C_2H_4COOH)_2 \quad (II)$$

wherein R is a $C_8$ to $C_{24}$ hydrocarbon.

11. The composition of claim 10 which comprises greater than about 40 wt % of N-alkyl-beta aminopropionic acid (I) based on total solids.

12. The process of claim 1 wherein the cation of said alkali metal hydroxides is selected from the group consisting of sodium, lithium, barium, magnesium, calcium, potassium and mixtures thereof.

13. A selective process for the preparation of N-alkyl-beta iminodipropionic acid (II)

$$RNH(C_2H_4COOH)_2 \quad (II)$$

wherein R is a $C_8$ to $C_{24}$ hydrocarbon, said process comprising reacting, in aqueous media, an alpha, beta- unsaturated carboxylic acid employed in a molar excess of from about 5 to about 30 with the corresponding primary amine of the formula $R_1NH2$ wherein $R_1$ is a fatty group having 8 to 24 carbon atoms, in the presence of an organic or inorganic base having a pKb of >1<15, whereby said acid is initially added to said aqueous media, the molar excess of acid is neutralized by addition of said base, followed by addition of said amine over time, the pH of the reaction being maintained in a range of from about 3.5 to 5.0.

14. The process of claim 13 wherein the pH is maintained in a range of from about 4 to 5.

15. The process of claim 13 wherein the acid is selected from the group consisting of acrylic acid, crotonic acid, isocrotonic acid, methacrylic acid, sorbic acid, cinnamic acid, maleic acid, fumeric acid, angelic acid, itaconic acid and mixtures thereof.

16. The process of claim 1 wherein $R_1$ is a fatty group having from 12 to 22 carbon atoms.

17. The process of claim 13 wherein the amine is selected from the group consisting of n-dodecylamine, n-hexadecylamine, n-octyldecylamine, cocoamine, tallowamine, hydrogenated tallowamine, partially hydrogenated tallowamine, oleylamine, erucylamine, behenylamine, lignocyrlamine and mixtures thereof.

18. The process of claim 13 wherein the base is selected from the group ammonia, hydroxylamine, diethylamine, methylamine, n-butylamine, glycine, aniline, alkali metal hydroxides, metal oxides and mixtures thereof.

\* \* \* \* \*

UNITED STATES PATENT AND TRADEMARK OFFICE
CERTIFICATE OF CORRECTION

PATENT NO. : 5,922,909
DATED : July 13, 1999
INVENTOR(S) : Lawrence J. Joffre

It is certified that error appears in the above-identified patent and that said Letters Patent is hereby corrected as shown below:

Title page,
Item [57], in formula (II), please change "RNH $(C_2H_4COOH)_2$" to
-- RN$(C_2H_4COOH)_2$ --.

Drawings,
Fig. 1, please change "Arrine" to -- Amine --.
Fig. 2, please change "Arrine" to -- Amine --.

Column 1,
Line 12, please change "surfactant fire" to -- surfactants are --.
Line 66, please change "Zwitterionic" to -- zwitterionic --.

Column 2,
Line 2, please change "hydrophobicity" to -- hydrophilicity --.
Line 7, please change "one formation" to -- the formation of --.
Line 14, please change "Zwitterionic" to -- zwitterionic --.
Line 28, please change "Zwitterionic" to -- zwitterionic --.
Line 40, in formula (II), please change "RNH $(C_2H_4COOH)_2$" to
-- RN$(C_2H_4COOH)_2$ --.
Line 44, please delete the parentheses before "corresponding".

Column 3,
Line 9, please change "hydrophobicity/hydrophobicity" to
-- hydrophobicity / hydrophilicity --.
Line 19, please change "applicants have" to -- the applicant has --.
Line 49, please change "hydrophobicity" to -- hydrophilicity --.

Column 4,
Line 23, please change "mixture" to -- mixtures --.
Line 51, please change "tie" to "the" and add -- the -- after "towards".

Column 5,
Line 8, please add -- : -- after the word "ether".
Line 9, please add -- : -- after the word "amphoteric".

UNITED STATES PATENT AND TRADEMARK OFFICE
CERTIFICATE OF CORRECTION

PATENT NO.    : 5,922,909
DATED         : July 13, 1999
INVENTOR(S)   : Lawrence J. Joffre It is certified that error appears in the above-identified patent and that said Letters Patent is hereby corrected as shown below:

Column 8,
Line 3, please change "$R_1NH2$" to -- $R_1NH_2$ --.
Line 38, please change "acids" to -- acid --.
Lines 42 and 53, in formula (II), please change "$RNH\ (C_2H_4COOH)_2$" to -- $RN(C_2H_4COOH)_2$ --.
Line 59, please change "$R_1NH2$" to -- $R_1NH_2$ --.
Line 64, please change "_" to -- and --.

Signed and Sealed this

Twenty-fifth Day of February, 2003

JAMES E. ROGAN
*Director of the United States Patent and Trademark Office*